(12) United States Patent
Kiene et al.

(10) Patent No.: US 6,715,870 B2
(45) Date of Patent: Apr. 6, 2004

(54) METHOD AND APPARATUS FOR PRINTING ONTO CASSETTES OR SPECIMEN SLIDES FOR HISTOLOGICAL PREPARATIONS

(75) Inventors: Uwe Kiene, Nussloch (DE); Manfred Biehl, Meckesheim (DE); Andreas Laudat, Meckesheim (DE); Holger Metzner, Nussloch (DE); Rolf Metzner, Dossenheim (DE); Roland Walter, Altlussheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 65 days.

(21) Appl. No.: 10/106,159

(22) Filed: Mar. 26, 2002

(65) Prior Publication Data

US 2002/0167577 A1 Nov. 14, 2002

(30) Foreign Application Priority Data

Mar. 27, 2001 (DE) .......................... 101 15 065

(51) Int. Cl.⁷ ................................. B41J 2/01
(52) U.S. Cl. ..................................... 347/102
(58) Field of Search ............... 347/102, 2, 150; 422/915; 219/210; 34/60

(56) References Cited

U.S. PATENT DOCUMENTS 5,568,173 A * 10/1996 Leenders et al. ............. 347/96
5,821,115 A 10/1998 Graupner
6,572,824 B1 * 6/2003 Ostgaard et al. ............. 422/67

FOREIGN PATENT DOCUMENTS

GB 2 206 083 A 12/1988
GB 2 235 163 A 2/1991

OTHER PUBLICATIONS

Hoffman, William; "Declaration of William Hoffman Regarding Automated Slide and Cassette Printers" in public use at Mayo Clinic, Rochester, MN since 1990.

"Embedding And Sectioning Methods For Microscope Preparation", Ernst Leitz GmbH, List 530–18a, Sep. 1973, (No translation—all references are discussed in specification).

* cited by examiner

Primary Examiner—Michael S Brooke
(74) Attorney, Agent, or Firm—Hodgson Russ LLP

(57) ABSTRACT

A method and an apparatus for printing onto plastic cassettes for histological preparations and/or onto glass specimen slides for microscopic thin sections are described, in which a computing device (1) is provided to control the printing device (2), and the printing device (2) comprises an inkjet printer for printing onto the cassettes and/or specimen slides. The ink is pre-dried by way of a hot-air drier (3) and completely dried by way of a flash device (4).

14 Claims, 2 Drawing Sheets

METHOD AND APPARATUS FOR PRINTING ONTO CASSETTES OR SPECIMEN SLIDES FOR HISTOLOGICAL PREPARATIONS

CROSS REFERENCE TO RELATED APPLICATIONS

This application claims priority of the German patent application 101 15 065.2 filed Mar. 27, 2001 which is incorporated by reference herein.

FIELD OF THE INVENTION

The invention concerns a system for printing onto plastic, in particular plastic cassettes for histological preparations, and/or onto glass, in particular glass specimen slides for microscopic thin sections.

BACKGROUND OF THE INVENTION

For the microscopic observation of preparations, in particular histological preparations, the latter must first be subjected to a chemical treatment in which the water contained in the specimen is removed and is replaced, for example, by paraffin or another medium. For this chemical treatment, the specimens are introduced into plastic cassettes. A cassette of this kind is depicted and described in, for example, U.S. Pat. No. 5,821,115 A.

Formulas for this kind of specimen treatment are known, for example, from the document "Embedding and sectioning methods for microscopic preparations [Einbettung- und Schneideverfahren für mikroskopische Präparate], Ernst Leitz GmbH, Liste 530-18a, September 1973." The preparation methods described are characterized in that water is removed from the preparation with ethanol/ethyl ether/propanol, and the preparation is then embedded in paraffin/methacrylate. It is understood that the plastic cassettes and the materials that are used must not react with the chemical reagents.

In this treatment, the specimens are stabilized to the extent that by means of a microtome, thin sections of the specimens can be made and can then each be mounted onto a glass specimen slide. Depending on the examination method, several thin sections are made of each preparation and are mounted onto the specimen slides. Prior to the actual microscopic observation, the preparations mounted onto the specimen slides must also be stained. It is usual in this context that not all preparations go through the same staining process, but instead that depending on the examination method, three or more differently stained preparations are produced.

For differentiation and identification, the individual cassettes and specimen slides must be given a label or code. It was hitherto usual to label the cassettes and specimen slides manually in pencil. Graphite was the only medium that was resistant to the reagents of the embedding process, but with the disadvantage that it cannot be applied in smudgeproof fashion. With manual labeling of the cassettes and/or specimen slides, however, errors can occur which then result in medical misdiagnoses.

For this reason, computer-assisted labeling systems have been developed which have largely eliminated these manual labeling errors. The difficulty that exists with these labeling systems is that of finding a suitable printing or writing medium. This medium must be characterized in that it resists a wide variety of chemical solvents and reagents, and adheres securely both to the plastic cassettes and to the glass of the specimen slide or the coated portion of the specimen slide. In addition, there is very little room on the cassettes and specimen slides for a corresponding code, so that the code must be applied in correspondingly delicate fashion.

GB Patent 2 206 083 discloses an "engraving machine" for a specimen slide and/or a cassette. This engraving device is controlled via a computer and an interface, and allows corresponding markings to be scratched into the cassette or specimen slide. It is disadvantageous, however, that this machine is very loud and very slow in operation, and also produces a great deal of debris due to the engraving. The engraved code is moreover very difficult to read.

GB Patent 2 235 163 A discloses a plotter for plastic cassettes in which labeling is performed with a thermal method using a heatable plotter pin and a carbon ribbon. The disadvantage here is that this method can be applied only to plastic, and moreover that only low resolution and a low printing speed can be achieved. The low printing speed results from the fact that the pin must move to each letter individually in the manner of a plotter.

In all known printing systems the resolution is relatively poor, so that only a very "coarse" code can be applied. It is thus not possible to realize the applied code in machine-readable fashion. The application of very thin lines, such as is necessary e.g. for barcodes, is not feasible with any of the known printing devices.

SUMMARY OF THE INVENTION

It is therefore the object of the present invention to develop a method and an apparatus for computer-assisted printing onto plastic cassettes and/or glass specimen slides in which not only high printing resolution but also a high printing speed are achieved.

The method for printing onto plastic cassettes for histological preparations and/or for printing onto glass specimen slides for microscopic thin sections is characterized in that the cassettes and/or specimen slides are conveyed to a printing device where a code is applied with a computer-controlled inkjet printer. In a further method step, the applied ink is then pre-dried with a flow of hot air. After this pre-drying, the applied ink is exposed to the light of a flash lamp and the ink is completely dried. The light of the flash lamp causes the liquid constituents of the ink to be abruptly heated and evaporated. Without a pre-drying of the ink by the flow of hot air, the abrupt evaporation would cause carbon particles in the ink to be carried off and deposited as a coating on the flash lamp.

In a further embodiment of the invention, after complete drying of the applied ink the cassette and/or specimen slide is transported to an output and/or stacking device where it is deposited.

The method is also characterized in that by way of an input unit, for example a barcode reader, a code can be read in and/or can be manually inputted by way of a keyboard; and said code is processed by the computing device and corresponding printing signals are then forwarded to the print head. The computing device can also be used to call up stored printing profiles (e.g. printing various data onto a plurality of specimen slides) with the code that is inputted or read in, and to forward corresponding printing signals to the printing device.

The apparatus for carrying out the method is characterized in that a computer is provided to control the printing device, and the printing device comprises an inkjet printer for printing onto the cassettes and/or specimen slides.

A solvent-based ink having carbon black pigments is used as the ink for the printing device. The ink is characterized in that it can be cured by abrupt thermal input with IR and UV radiation.

For complete drying and curing, the cassettes and/or specimen slides are first exposed to a flow of hot air and then transported into a flash lighting device. The flash light causes the pre-dried ink to be abruptly exposed to a heat input with IR and UV radiation, and thereby completely dried.

The invention is also characterized in that a material delivery device for cassettes of various dimensions and/or specimen slides of various dimensions is provided, so that different cassettes and/or specimen slides can be printed onto in computer-controlled fashion.

It has proven to be advantageous in this connection if the cassettes and/or specimen slides are grouped into stack magazines. The respective magazines can then be activated via the computing device. Different cassettes and/or different specimen slides can thus be printed onto in a single working step.

In a further embodiment of the invention, a transport device is provided for computer-controlled removal from the stack magazines and for delivery of the cassettes and/or specimen slides to the printing device.

The printing device is furthermore equipped with a removal device for deposition of the imprinted cassettes and/or imprinted specimen slides. This removal device is adjacent to the flash device.

The invention is also characterized in that the various devices can be activated simultaneously by the computer, so that different processes can be executed simultaneously within the printing device. A continuous flow of material is thus implemented, and the processing speed is considerably increased.

For acquisition and management of the specimen data, an input device is associated with the computer system. The data for controlling the entire printing system can thus be calculated by way of the inputted data, and the individual stations within the printing system can be activated simultaneously.

In a further embodiment of the invention, provision is made for the computer to be connected via an interface to a higher-level computing system, and for data to be exchanged between the two computing systems by way of said interface. This makes it possible for the data necessary for printing to be stored centrally and to be retrievable by a variety of printing systems. It is moreover also possible in this fashion to check whether the imprinted cassettes and/or specimen slides have already been completed.

It is also provided that the cassettes and/or specimen slides can be manually placed into the printing device.

BRIEF DESCRIPTION OF THE DRAWINGS

The invention will be presented in an exemplary embodiment and explained in more detail with reference to the schematic drawings, in which.

DETAILED DESCRIPTION OF THE INVENTION

Figure 1:
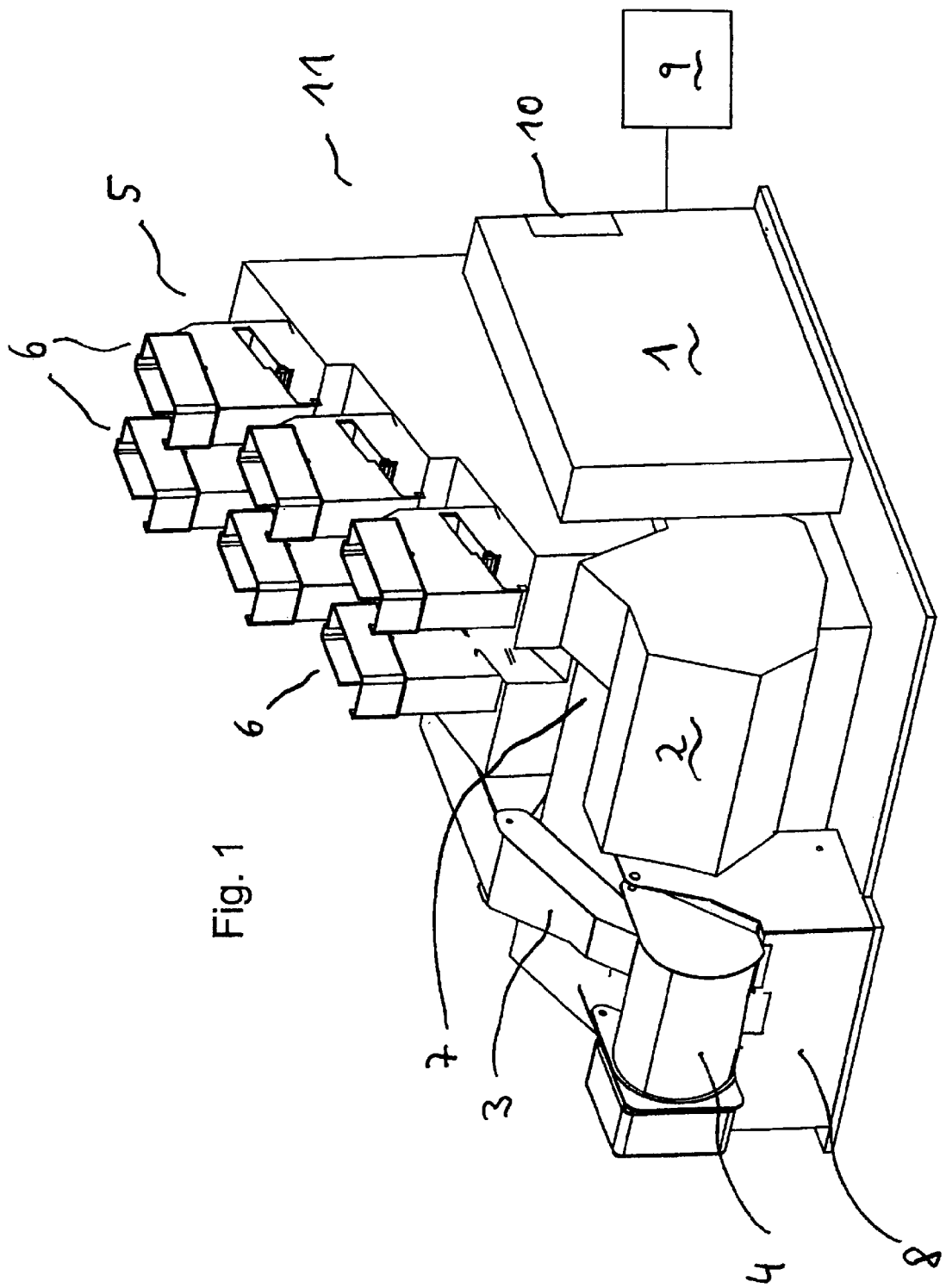
FIG. 1 is a perspective view of a printing device of the present invention.

FIG. 1 shows a printing system 11 having a material delivery system 5 which comprises multiple stack magazines 6 for the cassettes and/or specimen slides that are to be printed onto. Associated with material delivery system 5 is a transport device 7 that transports the cassettes and/or specimen slides to a printing device 2. Printing device 2 is equipped with an inkjet printer. The imprinted cassettes and/or specimen slides are forwarded, using transport device 7, to a hot-air drier 3. This hot-air drier generates a heated flow of air and directs it onto the imprinted surface of the cassette or specimen slide. The ink is pre-dried by the flow of hot air. The cassette and/or specimen slide is then forwarded to a flash device 4 and the imprinted surface is exposed to the flash light. There the pre-dried ink is abruptly exposed to a thermal input with IR and UV radiation by way of the flash light, and thereby completely dried.

The cassettes and/or specimen slides treated in this fashion are then forwarded via transport device 7 to a removal device 8.

A computing device 1 is provided to control printing system 11. Computing device 1 comprises an interface 10 for connection to a higher-level computing system. Computing system 1 is furthermore connected to an input device 9; the latter can comprise both a barcode reader and an input keyboard.

The individual units can be controlled simultaneously by computing device 1, so that multiple cassettes and/or specimen slides can be processed simultaneously in printing system 11, thus ensuring a continuous material flow.

Figure 2:
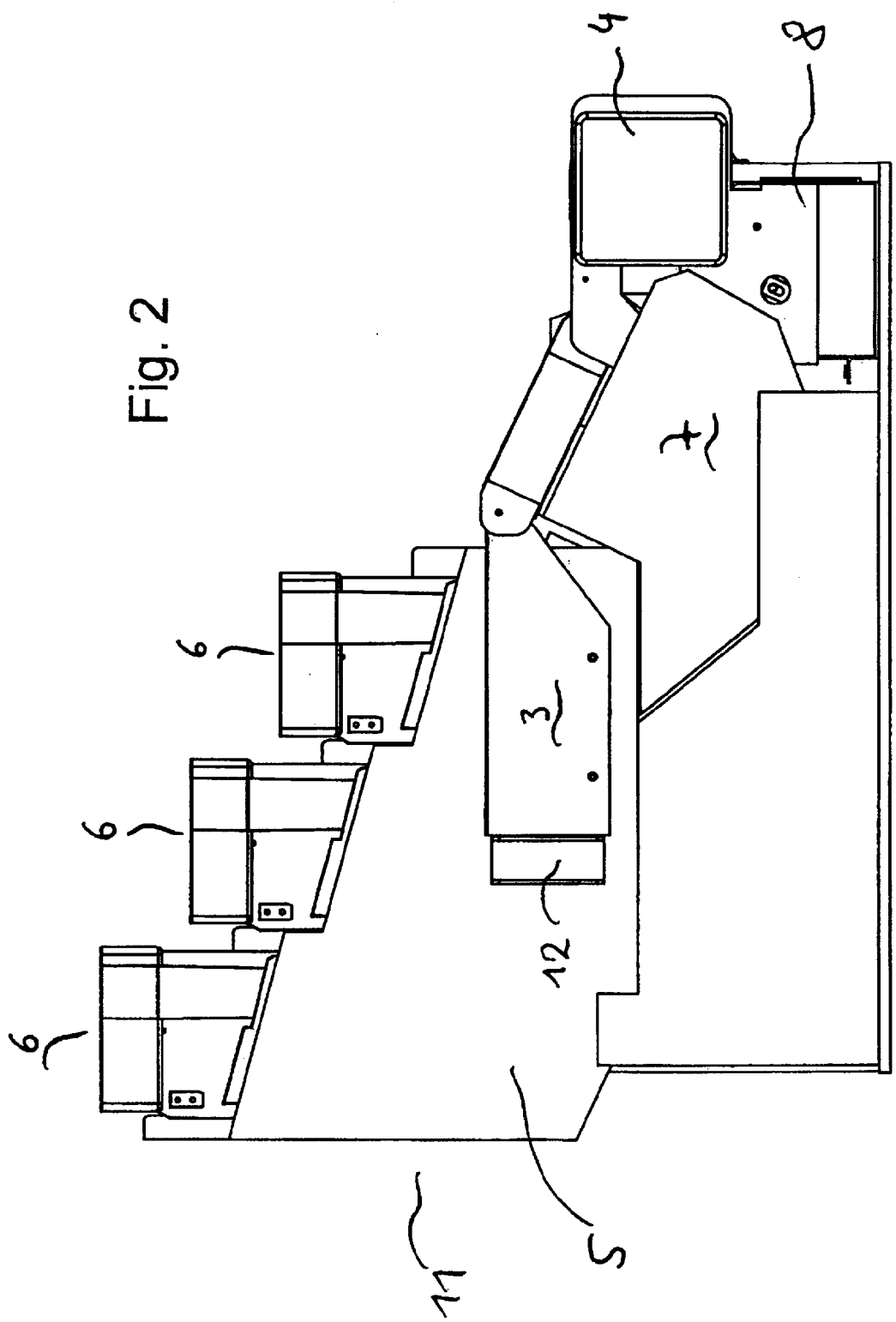
FIG. 2 is a side elevational view of the printing device.

FIG. 2 shows a side view of printing system 11 with material delivery device 5 and stack magazines 6. Hot-air drier 3 comprises a fan with heating coil 12 with which the continuous flow of hot air is generated.

With the printing system, both cassettes of different dimensions and specimen slides can be selectably and alternatingly printed onto. It is thus also possible to print onto both cassettes and specimen slides in one working step. Provision can of course also be made for equipping the printing system only for printing onto cassettes or only for printing onto specimen slides.

Parts List
   1 Computing device
   2 Printing device
   3 Hot-air drier
   4 Flash device
   5 Material delivery device
   6 Stack magazine
   7 Transport device
   8 Removal device
   9 Input device
   10 Interface
   11 Printing system
   12 Fan with heating coil

What is claimed is:

1. A method for printing onto plastic cassettes for histological preparations and/or for printing onto glass specimen slides for microscopic thin sections, in which the cassettes and/or specimen slides are conveyed to a printing device where a code is applied thereto, said method comprising the steps of:

applying said code using an inkjet printer controlled by a computer exposing said cassettes and/or specimen slides to a flow of hot air after said code is applied to pre-dry ink applied by said inkjet printer; and exposing said applied ink to light produced by a flash lamp after said applied ink is pre-dried by said flow of hot air to completely dry said applied ink.

2. The method as defined in claim 1, further comprising the step of:

transporting said cassettes and/or specimen slides to an output device after said applied ink has been completely dried.

3. The method as defined in claim 2, wherein said output device is a stacking device.

4. The method as defined in claim 1, further comprising the steps of:
inputting said code to said computer;
processing said code by means of said computer to provide printing signals for printing said code; and
forwarding said printing signals to said inkjet printer.

5. The method as defined in claim 1, further comprising the step of using said computer to control a means for conveying said cassettes and/or specimen slides to said printing device to provide a continuous flow of cassettes and/or specimen slides through said printing device.

6. An apparatus for printing onto plastic cassettes for histological preparations and/or onto glass specimen slides for microscopic thin sections, said apparatus comprising:
a printing device including an inkjet printer for printing onto said cassettes and/or specimen slides, wherein said inkjet printer uses a solvent-based ink having carbon black pigments and wherein said ink can be dried by abrupt thermal input with infrared and ultraviolet radiation;
a computer connected to said printing device for controlling said printing device; and
a hot air drier and a flash device for curing said ink printed on said cassettes and/or specimen slides, wherein the ink is pre-dried by exposure to a flow of hot air from the hot air drier and then completely dried by exposure to the flash device.

7. The apparatus as defined in claim 6, further comprising a material delivery device for supplying cassettes of various dimensions and specimen slides of various dimensions to said printing device.

8. The apparatus as defined in claim 7, wherein said material delivery device includes a plurality of stack magazines into which said cassettes and/or specimen slides are grouped.

9. The apparatus as defined in claim 8, wherein said material delivery device includes a transport device connected to said computer for computer-controlled removal of cassettes and/or specimen slides from said stack magazines and for delivery of said removed cassettes and/or specimen slides to said printing device.

10. The apparatus as defined in claim 6, further comprising a removal device arranged after said flash device for depositing imprinted cassettes and/or imprinted specimen slides.

11. The apparatus as defined in claim 6, further comprising an input device connected to said computer for acquisition of specimen data.

12. The apparatus as defined in claim 11, wherein data for controlling said printing device are calculated by said computer based on said inputted specimen data.

13. The apparatus as defined in claim 6, wherein said cassettes and/or specimen slides can be manually delivered to said printing device.

14. An apparatus for printing onto plastic cassettes for histological preparations and/or onto glass specimen slides for microscopic thin sections, said apparatus comprising:
a printing device including an inkjet printer for printing onto said cassettes and/or specimen slides;
a computer connected to said printing device for controlling said printing device;
a hot air drier and a flash device for curing said ink printed on said cassettes and/or specimen slides; and
a material delivery device for supplying cassettes of various dimensions and specimen slides of various dimensions to said printing device, said material delivery device including a plurality of stack magazines into which said cassettes and/or specimen slides are grouped and a transport device connected to said computer for computer-controlled removal of cassettes and/or specimen slides from said stack magazines and for delivery of said removed cassettes and/or specimen slides to said printing device;
wherein said printing device, said hot air drier, said flash device, said material delivery device, said plurality of stack magazines, and said transport device are connected to said computer and can be activated simultaneously by said computer;
whereby different processes can be executed simultaneously.

* * * * *